United States Patent [19]

Wade

[11] Patent Number: 4,962,252
[45] Date of Patent: Oct. 9, 1990

[54] PROCESS FOR THE PRODUCTION OF ALKENYL-SUBSTITUTED BENZENE DERIVATIVES

[75] Inventor: Steven R. Wade, Surrey, England

[73] Assignee: The British Petroleum Company p.l.c., London, England

[21] Appl. No.: 384,916

[22] Filed: Jul. 25, 1989

Related U.S. Application Data

[63] Continuation of Ser. No. 300,487, Jan. 23, 1989, abandoned.

[30] Foreign Application Priority Data

Feb. 6, 1988 [GB] United Kingdom ................ 8802731

[51] Int. Cl.$^5$ ............................................. C07C 15/46
[52] U.S. Cl. ................................... 585/438; 585/435; 585/443; 585/428; 585/500
[58] Field of Search ............... 585/428, 435, 438, 443, 585/500

[56] References Cited

U.S. PATENT DOCUMENTS 4,769,508 9/1988 Gastinger et al. .

FOREIGN PATENT DOCUMENTS 0206044 12/1986 European Pat. Off. .
0230769 8/1987 European Pat. Off. .
2829386 1/1979 Fed. Rep. of Germany .

OTHER PUBLICATIONS

Proceedings of the 11th World Petroleum Congress 1985 vol. 4 pp. 465–471 Khcheyan et al.

Primary Examiner—Helen Sneed
Assistant Examiner—James Saba
Attorney, Agent, or Firm—Brooks Haidt Haffner & Delahunty

[57] ABSTRACT

Alkenyl-substituted benzene derivatives are produced by oxidatively coupling at elevated temperature a benzene having at least one activated saturated hydrocarbyl substituent in vapor form with a gaseous paraffinic hydrocarbon in the presence of a gaseous oxidant and as catalyst therefor a binary metallic or multimetallic composition capable of oxidatively coupling methane.

7 Claims, No Drawings

PROCESS FOR THE PRODUCTION OF ALKENYL-SUBSTITUTED BENZENE DERIVATIVES

This application is a continuation, of application Ser. No. 07/300,487, filed Jan. 23, 1989, now abandoned.

The present invention relates to the production of alkenyl-substituted benzene derivatives, and in particular styrene, by the catalysed oxidative coupling of a paraffinic hydrocarbon, particularly methane, and benzene having at least one activated saturated hydrocarbyl substituent.

Styrene, for example, is a large tonnage chemical product. It is generally prepared on a commercial scale from benzene by alkylation with ethylene in the presence of a Friedel Crafts alkylation catalyst, for example aluminum (III) chloride, to produce ethylbenzene followed by dehydrogenation of the ethylbenzene over a noble metal catalyst, for example platinum, to convert ethylbenzene to styrene. Part of the benzene feedstock may be derived from toluene by oxidative demethylation. A desirable objective would be to simplify the process by eliminating one or more steps. Another desirable objective would be to replace ethylene, which is generally obtained from crude oil, as a reactant by methane, which is abundantly available.

It is already known, from U.S. Pat. No. 3,965,206 for example, that toluene and toluene derivatives can be dehydrocoupled to stilbene and stilbene derivatives in a vapour phase reaction in the presence of lead oxide. After purification of by-product polar impurities, stilbene can be catalytically reacted in the vapour phase with ethylene to produce styrene. This process does not fulfill the desirable objectives hereinbefore mentioned in the respects that it is arguably not simpler and does not avoid the dependence on ethylene.

In 'Proc 11th World Petroleum Congress, 1985, vol. 4', at pages 465 to 471, Khcheyan et al describe a process which to some extent meets the aforesaid objectives. The process involves high temperature (about 700° C.) interaction of $C_1$ to $C_4$ alkanes such as methane with compounds containing a methyl group at the alpha-position on the electron-accepting functional group. The process proceeds in a medium with excess alkane in the presence of oxygen to give products with new C—C and C=C bonds. The cleavage of the C—C bond of the starting hydrocarbon is a side route which gives demethylation products. With a starting hydrocarbon conversion of 30-50%, selectivity to products with new C—C and C=C bonds is reportedly from 60-90 mol % of theoretical. The reaction is applicable to nitriles, aromatics and some olefin compounds. Natural gas is a preferred methylating agent. Petrochemicals such as styrene, acrylonitrile, isoprene and divinyl can be produced by the process. The process described with respect to toluene is a homogeneous (uncatalysed) reaction.

Finally, in Russian Patent No. 1074854 Khcheyan et al discloses the reaction of toluene with $C_1$ to $C_4$ alkanes in the presence of oxygen or an oxygen-containing gas, iron or titanium oxides at 600°-800° C. distinguished by the fact that, in order to increase process yield, the process is carried out at pressures of 0.7-15 atmospheres in the presence of hydrogen peroxide and/or tert-butyl peroxide in an amount of 0.001-1.0 wt % of the mass of the initial toluene.

It is also well-known that methane can be oxidatively coupled in the presence of a variety of oxidative coupling catalysts to produce higher hydrocarbons including ethylene, Thus, for example, our EP-A-0230769 describes the production of higher hydrocarbons from methane by reacting the methane at elevated temperature with an oxygen-containing gas having a ratio of methane to oxygen greater then the stoichiometric ratio for complete combustion in the presence as catalyst of a lithium-doped material which under the reaction conditions is a base-stable, non-melting, oxygen-stable compound of an element of Groups III to VIII of the Periodic Table.

The iron or titanium oxide catalysts of the aforesaid Russian Patents No. 1074854 are not, in the absence of other metals, generally regarded as effective methane oxidative coupling catalysts and our own work on the reaction of methane and toluene in the absence of peroxides would tend to support this conclusion. In the latter reaction, rather than catalyse the coupling reaction to produce styrene (and ethylbenzene, a product valuable as a styrene precursor), they tend to catalyst deep oxidation, decomposition and dealkylation side reactions. In contrast, we have unexpectedly, found that binary metallic and multimetallic methane oxidative coupling catalysts favour the coupling reaction, i.e. are more selective to styrene (and ethylbenzene).

Accordingly, the present invention provides a process for the production of an alkenyl-substituted benzene derivative by oxidatively coupling at elevated temperature a benzene having at least one activated saturated hydrocarbyl substituent in vapour form with a gaseous paraffinic hydrocarbon in the presence of a gaseous oxidant and a catalyst therefor characterised in that the catalyst comprises a binary metallic or multimetallic composition capable of oxidatively coupling methane.

The presence of a catalyst can facilitate the reaction allowing a greater range of process conditions and increased reaction control. Moreover, in the production of styrene, for example, from toluene and methane the formation of oxygenates can be substantially eliminated, thereby avoiding the need for formaldehyde/benzaldehyde recycle and the formation of phenols and xylenols can be avoided. Greater selectivity to desired hydrocarbon products can be achieved, together with easier separation of product liquids. An additional advantage of avoiding substantial formation of oxygenates is that waste treatment can be simplified, it being well known that oxygenates tend to contaminate water, which is a by-product of the process of the invention.

The use of a binary metallic or multimetallic methane oxidative coupling catalyst rather than iron oxide or titanium oxide as catalyst in the reaction provides the advantages that higher selectivities to styrene (and ethylbenzene) can be achieved without the need to use peroxides.

As one reactant there is used benzene having at least one activated saturated hydrocarbyl substituent. Suitable activated substituents include alkyl groups, for example $C_1$ to $C_4$ alkyl groups. A preferred activated substituent is a methyl group. The benzene reactant may be mono- or poly- substituted, for example di-substituted. Examples of suitable benzenes having at least one activating saturated hydrocarbyl substituent include toluene and the xylenes.

As the paraffinic hydrocarbon there may suitably be used either methane, ethane, propane, a butane, or a mixture of two or more thereof. It is preferred to use methane, which may be used in substantially pure form or in the form of a mixture with other gaseous paraffinic hydrocarbons. The methane may also contain, for example, minor amounts of one or more of carbon dioxide and nitrogen. A preferred methane-containing mixture is natural gas which may contain in addition to methane as the principal component, ethane and propane and possibly also carbon dioxide and nitrogen. It is preferred to employ an excess of the gaseous paraffinic hydrocarbon reactant over the benzene reactant in order to avoid self-condensation of the benzene reactant.

As the catalyst there may be used any binary metallic or multimetallic composition capable of oxidatively coupling methane, of which many are known in the art. A preferred class of catalyst is a binary metallic or multimetallic combination containing at least one alkali metal or an alkaline earth metal or compounds thereof and at least one metal oxide from groups II to VIII of the Periodic Table of the Elements including the rare earth elements. Preferred alkali and alkaline earth metals include lithium and sodium or compounds thereof, preferably as either carbonates or halides. A specific example of this type of catalyst is a lithium-doped material which under the reaction conditions is a physically base-stable, non-melting, oxygen-stable compound of an element of Groups III to VIII of the Periodic Table of the Elements including the rare earth elements as described in our copending EP-A-0230769, the contents of which are incorporated by reference herein. Another specific example is a lithium-doped magnesium oxide, promoted with for example sodium carbonate. Another preferred class of catalyst is manganese oxide, preferably trimanganese tetroxide, incorporating at least one of the elements aluminium, tin, titanium, tungsten, tantalum, silicon, germanium, lead, phosphorus, arsenic, antimony, boron, gallium, iridium, lanthanides and actinides, promoted with at least one alkali metal halide, as described in our copending European application No. 88309672.9 (BP Case No. 6816).

The catalysts may be employed either supported or unsupported. Suitable supports include silica, magnesia, alumina, titania, zirconia and combinations thereof.

As the gaseous oxidant there may be used either a molecular oxygen-containing gas or a nitrogen-containing oxidant gas, or both. Preferably the gaseous oxidant is a molecular oxygent-containing gas, more preferably oxygen. As the molecular oxygen-containing gas there may be used either substantially pure oxygen, air or an air/oxygen mixture. The nitrogen-containing oxidant gas may be, for example, dinitrogen monoxide.

The gaseous oxidant may either be fed pre-mixed with the gaseous paraffinic hydrocarbon or added in stages to the reaction.

There may also be present a source of halogen or sulphur which is preferably either chlorine or bromine or a compound thereof, for example hydrogen chloride or $SO_2$ or $H_2S$. The source of halogen or sulphur may be fed either continuously or intermittently.

The conditions under which the process is operated will depend upon a number of factors including the nature of the reactants and the nature of the catalyst. Typically the temperature may be in the range from 500° to 1000° C., for example 600° to 900° C. Optimum operating temperatures within the aforesaid range will depend on the nature of the catalyst, for example whereas a $Li_2CO_3/Na_2CO_3/MgO$ catalyst is not very active for methane/toluene oxidative coupling to styrene at 650° C., at 700° C. its activity is very much increased. The optimum operating temperature for each individual catalyst may readily be determined by experiment. The pressure may be in the range from 0 to 100 bar, for example from 1 to 30 bar. The process is preferably operated in a continuous manner at a Gas Hourly Space Velocity (GHSV) typically in the range from 100 to 100,000 $h^{-1}$, for example from 1000 to 6000 $h^{-1}$.

In a preferred embodiment, the present invention provides a process for the production of styrene which process comprises contacting toluene in vapour form, gaseous methane and gaseous oxygen with a coupling catalyst as hereinbefore described.

In addition to styrene the liquid product also contains benzene and ethylbenzene, which together with styrene can total up to 88% of the product. The gaseous product principally comprises carbon dioxide and unreacted methane together with minor amounts of carbon monoxide and $C_2$ hydrocarbons. The nature of the products is such that methane separation and recycle should be relatively inexpensive. The aqueous product can contain less than 0.1% wt of organic materials.

The process of the present invention will now be further illustrated by reference to the following Examples and Comparison Tests. A tubular stainless steel reactor was employed in all the Examples and Tests. In Examples 1 to 7 and 9 and Comparison Tests 3 to 5 a $Li_2/CO_3/Na_2CO_3/MgO$ catalyst was employed. 10 ml of 350–600 micron catalyst pellets were used. The gaseous product was analysed using a Pye Unicam PU 4500 multicolumn gas chromatograph. The liquid product was analysed using a WCOT fused silica/CP Cil-5 CB capillary column.

CATALYST PREPARATION (A) 50 gm MgO (BDH) was dry mixed with 13.2 g lithium carbonate and 18.9 g sodium carbonate. Sufficient distilled water was added to form a smooth paste, which was triturated in a pestle and mortar. The paste was dried at 125° C., broken up, and calcined in air at 800° C. for 6 hours.

The catalyst was pre-treated by running under reaction conditions for 1 hour prior to any test period.

(B) 40 g $Mn_3O_4$ (produced by calcining BDH GPR grade $MnO_2$ at 100° C./air for 8 hours) was dry-mixed with 45.5 g acid washed silica dust (less than 150 microns particle size) and impregnated with a solution of 10.21 g sodium chloride in water. Sufficient additional water was added to form a smooth paste, which was dried at 125° C., broken up and calcined in air for 90 minutes at 750° C.

COMPARISON TESTS 1 AND 2

Toluene, methane and oxygen were passed through an empty tube in the proportions and under the conditions shown in Table 1 in an attempt to repeat the homogeneous experiments reported by Khcheyan et al.

Benzaldehyde and benzene were the major products. These Tests are not according to the invention because no catalyst was used.

EXAMPLES 1 TO 7

Toluene, methane and oxygen were contacted with catalyst (A) under a variety of conditions as shown in Table 1.

COMPARISON TESTS 3 TO 5

Toluene, methane and nitrogen were contacted with catalyst (A) under the conditions shown in Table 1.

These Tests are not according to the present invention because methane was omitted.

COMPARISON TESTS 6 AND 7

Toluene, methane and oxygen were contacted with catalysts under the conditions shown in Table 1 using a stainless steel reactor (12.8 mm internal diameter). The catalysts used (10 ml, 355-600 microns particle size) were in Comparison Test 6 iron oxide ($Fe_2O_3$) and in Comparison Test 7 titanium oxide.

These tests are not according to the present invention because no oxidative coupling catalyst as defined by the present invention was used.

Comparing the results of Examples 5-7 with those of Comparison Tests 2,4,6 and 7, the coupling yields (as defined by the product of toluene conversion to liquids and the selectivity of styrene/ethylbenzene/xylenes × 100) for the Examples are all equal to or greater than 10 whereas those for the Comparison Tests are all less than 5 and the decomposition/coupling ratios (as defined by the ratio of decomposition products (benzene) to coupling products (styrene, ethylbenzene, xylenes)) for the Examples are all less than or equal to 1, whereas for the Comparison Tests they are all greater than about 2 and as high as 42.5 for Comparison Test 2.

The results of Examples 1 to 7 and Comparison Tests 1 to 7 are given in Table 2.

EXAMPLE 8

Toluene, methane and oxygen were contacted with Catalyst (B) under the conditions shown in Table 3.

The results are given in Table 4.

EXAMPLE 9

Toluene and propane were contacted with Catalyst (A) under the conditions shown in Table 3 with staged addition of oxygen.

The results are given in Table 4.

TABLE 1

| Example | Feed Vol % CH$_4$ | O$_2$ | C$_7$H$_8$ | N$_2$ | GHSV h$^{-1}$ | Furn Temp °C. | Max Bed Temp °C. |
|---|---|---|---|---|---|---|---|
| CT 1 | 87.0 | 8.7 | 4.2 | — | 5625 | 700 | 715 |
| CT 2 | 79.4 | 15.6 | 5.0 | — | 6160 | 750 | 769 |
| 1 | 80.2 | 14.8 | 4.9 | — | 6250 | 650 | 644 |
| 2 | 80.2 | 14.8 | 4.9 | — | 6250 | 700 | 917 |
| 3 | 78.6 | 14.5 | 6.9 | — | 6406 | 700 | 924 |
| 4 | 71.1 | 14.8 | 14.0 | — | 1490 | 800 | 784 |
| 5 | 82.5 | 9.3 | 8.1 | — | 2538 | 750 | 753 |
| 6 | 77.6 | 14.8 | 7.7 | — | 2686 | 750 | 773 |
| 7 | 71.6 | 21.2 | 7.2 | — | 2861 | 750 | 850 |
| CT 3 | — | 9.0 | 8.2 | 82.7 | 2497 | 750 | 756 |
| CT 4 | — | 15.3 | 7.8 | 76.9 | 2647 | 750 | 781 |
| CT 5 | — | 20.9 | 71.1 | 72.0 | 2889 | 750 | 856 |
| CT 6 | 78.5 | 14.7 | 6.8 | — | 3015 | 725 | 758 |
| CT 7 | 78.9 | 14.3 | 6.8 | — | 2985 | 725 | 813 |

CT = Comparison Test

TABLE 2

| Example | Toluene$^a$ Conversion to Liquid Products (%) | Benzene | Ethyl Benzene | Styrene | Xylenes | Benz-aldehyde | Higher Products |
|---|---|---|---|---|---|---|---|
| CT 1 | 5.7 | 53.9 | 10.1 | 6.9 | 1.4 | 26.3 | 1.4 |
| CT 2 | 4.2 | 93.5 | 2.2 | 0 | 0 | 2.2 | 2.1 |
| 1 | 3.3 | 40.1 | 21.2 | 1.9 | 1.7 | 14.2 | 20.9 |
| 2 | 29.1 | 35.6 | 27.5 | 28.9 | 0.7 | 0 | 7.3 |
| 3 | 25.6 | 25.8 | 36.6 | 25.7 | 90.8 | 0 | 11.1 |
| 4 | 10.7 | 22.7 | 25.6 | 20.3 | 0 | 0 | 31.4 |
| 5 | 13.7 | 17.1 | 51.8 | 19.2 | 3.2 | 0 | 8.7 |
| 6 | 18.8 | 16.1 | 43.8 | 25.2 | 2.2 | 0 | 12.7 |
| 7 | 25.2 | 29.0 | 33.6 | 26.1 | 2.1 | 0 | 9.2 |
| CT 3 | 9.2 | 23.9 | 10.2 | 10.2 | 0.6 | 0 | 55.1 |
| CT 4 | 10.3 | 35.3 | 16.3 | 17.6 | 0.9 | 0 | 29.9 |
| CT 5 | 18.3 | 78.0 | 3.2 | 4.4 | 1.2 | 0 | 13.2 |
| CT 6 | 4.8 | 67.3 | 9.5 | 13.3 | 0.5 | — | 9.4 |
| CT 7 | 16.0 | 64.0 | 8.2 | 17.7 | 1.5 | — | 8.6 |

Toluene Oxidative Methylation
$^a$Conversion = moles product/moles toluene fed
$^b$Oxygen Conversion greater than 98 in all cases
CT = Comparison Test

TABLE 3

| Example | Feed Volume (%) Methane | Propane | Toluene | Oxygen | GHSV (h$^{-1}$) | Furn. Temp. (°C.) | Max. Bed Temp. (°C.) |
|---|---|---|---|---|---|---|---|
| 8 | 80.2 | — | 4.0 | 15.8 | 2920 | 750 | 781 |
| 9 | — | 61.9$^{(a)}$ | 7.8 | 30.2$^{(b)}$ | 3071 | 750 | $^{(b)}$ |

$^{(a)}$Included 4.1 vol % ethane present in the feed gas
$^{(b)}$Staged oxygen addition; therefore no maximum bed temperature recorded

TABLE 4

| Example | Toluene conversion to liquid prods (%) | Benzene | Ethyl benzene | Styrene | Xylenes | Benzal-dehyde | Higher Products |
|---|---|---|---|---|---|---|---|
| 8 | 47.8 | 18.9 | 20.4 | 34.5 | 1.2 | 9.8$^{(a)}$ | 15.2$^{(b)}$ |

TABLE 4-continued

| Example | Toluene conversion to liquid prods (%) | Liquid Products (mole %) | | | | | |
|---|---|---|---|---|---|---|---|
| | | Benzene | Ethyl benzene | Styrene | Xylenes | Benzaldehyde | Higher Products |
| 9 | 19.8 | 17.8 | 31.8 | 25.1 | 2.6 | 0 | 22.7(c) |

(a)Includes benzofurans (8.4 mol %)
(b)Includes chlorocarbons (0.3 mol %)
(c)Includes C3- and C4- substituted benzenes (18.4 mol %). Benzofurans and chlorocarbons are unwanted by-products, whereas C3- and C4- substituted benzenes are potentially useful products.

I claim:

1. A process for the production of an alkenyl-substituted benzene derivative by oxidatively coupling at elevated temperature a benzene having at least one activated saturated hydrocarbyl substituent in vapour form with a gaseous paraffinic hydrocarbon in the presence of a gaseous oxidant and a catalyst therefor wherein the catalyst is selected from (a) a lithium doped magnesium oxide promoted with sodium carbonate or (b) trimanganese tetroxide incorporating at least one of the elements aluminum, tin, titanium, tungsten, tantalum, silicon, germanium, lead, phosphorus, arsenic, antimony, boron, gallium and indium promoted with at least one alkali metal halide.

2. A process according to claim 1 wherein the saturated hydrocarbyl substituent is a $C_1$ to $C_4$ alkyl group.

3. A process according to claim 1 wherein the gaseous paraffinic hydrocarbon is either methane, ethane, propane, a butane or a mixture of two or more thereof.

4. A process according to claim 1 wherein the gaseous paraffinic hydrocarbon is methane.

5. A process according to claim 1 wherein the gaseous oxidant is a molecular oxygen-containing gas.

6. A process according to claim 5 wherein the molecular oxygen-containing gas is oxygen.

7. A process according to claim 1 wherein the benzene having at least one activated hydrocarbyl substituent is toluene, the gaseous paraffinic hydrocarbon is methane, the gaseous oxidant is oxygen and the alkenyl-substituted benzene derivative produced is styrene.

* * * * *